(12) United States Patent
Yamasaki (10) Patent No.: US 8,869,594 B2
(45) Date of Patent: Oct. 28, 2014

(54) PARTICLE DETECTING DEVICE EVALUATING SYSTEM AND PARTICLE DETECTING DEVICE EVALUATING METHOD

(71) Applicant: AZBIL Corporation, Tokyo (JP)

(72) Inventor: Shinsuke Yamasaki, Tokyo (JP)

(73) Assignee: AZBIL Corporation, Tokyo (JP)

( * ) Notice: Subject to any disclaimer, the term of this patent is extended or adjusted under 35 U.S.C. 154(b) by 0 days.

(21) Appl. No.: 13/644,960

(22) Filed: Oct. 4, 2012

(65) Prior Publication Data

US 2013/0081446 A1 Apr. 4, 2013

(30) Foreign Application Priority Data

Oct. 4, 2011 (JP) .................................. 2011-220084

(51) Int. Cl.
| | | |
|---|---|---|
| *G01N 21/01* | (2006.01) | |
| *G01N 15/06* | (2006.01) | |
| *G01N 21/53* | (2006.01) | |
| *G01N 15/00* | (2006.01) | |

(52) U.S. Cl.
CPC ................ *G01N 15/06* (2013.01); *G01N 21/53* (2013.01); *G01N 2015/0046* (2013.01); *G01N 2015/0693* (2013.01)
USPC .......................... 73/28.01; 73/863.01; 356/337

(58) Field of Classification Search
CPC .................. G01N 21/53; G01N 15/06; G01N 2015/0693; G01N 2015/0046
USPC .......... 356/432–444, 355–343; 250/573, 574, 250/575; 73/863.01, 28.01
See application file for complete search history.

(56) References Cited

U.S. PATENT DOCUMENTS

| | | | | | |
|---|---|---|---|---|---|
| 3,661,460 | A | * | 5/1972 | Elking et al. .................... | 356/36 |
| 4,794,086 | A | * | 12/1988 | Kasper et al. ................... | 436/36 |
| 4,938,592 | A | * | 7/1990 | Poole et al. .................... | 356/335 |
| 5,296,910 | A | * | 3/1994 | Cole ............................ | 356/28.5 |
| 5,311,290 | A | * | 5/1994 | Olson et al. ................... | 356/634 |
| 6,040,004 | A | * | 3/2000 | Matsumoto et al. ........... | 427/185 |
| 6,211,956 | B1 | * | 4/2001 | Nicoli ........................... | 356/337 |
| 6,639,670 | B2 | * | 10/2003 | Carpenter ..................... | 356/335 |
| 2009/0095053 | A1 | * | 4/2009 | Creek et al. .................. | 73/28.01 |
| 2009/0121165 | A1 | * | 5/2009 | Aroussi ........................ | 250/573 |

FOREIGN PATENT DOCUMENTS

| | | |
|---|---|---|
| JP | 2004-159508 | 6/2004 |
| JP | 2005-077251 | 3/2005 |
| JP | 2008-022764 | 2/2008 |
| JP | 2008-022765 | 2/2008 |

* cited by examiner

*Primary Examiner* — Sang Nguyen
(74) *Attorney, Agent, or Firm* — Troutman Sanders LLP (57) ABSTRACT

A particle detecting device evaluating system having a test chamber provided, in one face thereof, with a plurality of gas intake vents, where respective particle detecting devices are provided; an injecting device for injecting particles into the test chamber; a light sheet forming device for forming a light sheet within the test chamber; and an imaging device for imaging particles made visible by the light sheet.

16 Claims, 6 Drawing Sheets

PARTICLE DETECTING DEVICE EVALUATING SYSTEM AND PARTICLE DETECTING DEVICE EVALUATING METHOD

CROSS-REFERENCE TO PRIOR APPLICATION

This application claims priority to Japanese Patent Application No. 2011-220084, filed Oct. 4, 2011. This application is incorporated herein by reference in its entirety.

FIELD OF TECHNOLOGY

The present invention relates to an environment evaluating technology, and, in particular, relates to a particle detecting device evaluating system and a particle detecting device evaluating method.

BACKGROUND

In, for example, clean rooms in semiconductor manufacturing factories, the quantity of particles suspended in the air within the room is monitored using a particle detecting device. In evaluating the particle capturing performance of particle detecting devices, the correspondence between the quantity of particles actually dispersed in the air within the test environment and the results of detection by the particle detecting device is examined. (See, for example, Japanese Unexamined Patent Application Publication 2004-159508, Japanese Unexamined Patent Application Publication 2008-22764, Japanese Unexamined Patent Application Publication 2008-22765, and Japanese Unexamined Patent Application Publication 2005-77251.)

SUMMARY

One object of the present invention is to provide a particle detecting device evaluating system and a particle detecting device evaluating method enabling accurate evaluation of a particle detecting device.

A form of the present invention provides a particle detecting device evaluating system having (a) a test chamber wherein a plurality of gas intake vents, for which respective particle detecting devices are provided, is provided in one face thereof; (b) an injecting device for injecting particles into the test chamber; (c) a light sheet forming device for forming a light sheet within the test chamber along the plurality of gas intake vents; and (d) an imaging device for imaging particles that have been made visible by the light sheet.

Moreover, a form of the present invention provides a particle detecting device evaluating method including (a) disposing a particle detecting device at each of a plurality of gas intake vents that is provided on one face in a test chamber; (b) injecting particles into the test chamber; (c) forming a light sheet within the test chamber along the plurality of gas intake vents; (d) drawing in gas from within the test chamber, through each of the plurality of gas intake vents, by the particle detecting devices; and (d) imaging particles that are made visible by the light sheet.

The examples of the present invention enables the provision of a particle detecting device evaluating system and particle detecting device evaluating method, able to evaluate a particle detecting device accurately.

DETAILED DESCRIPTION

An example of the present invention is described below. In the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions.

Figure 1:
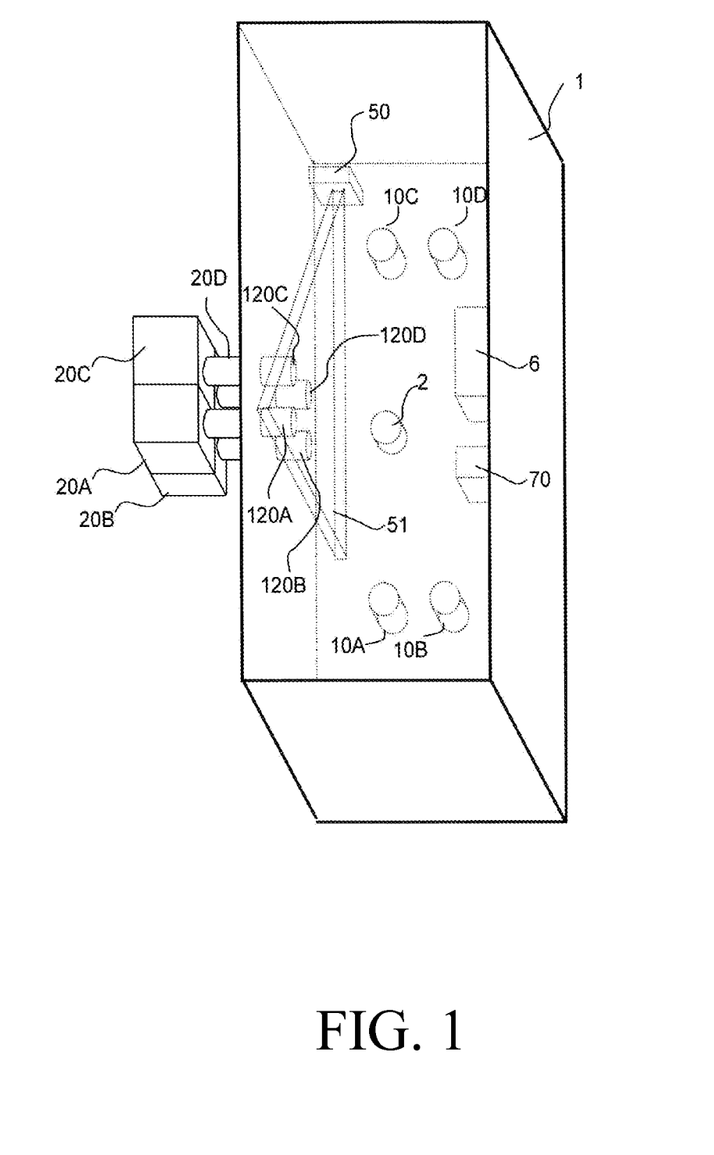
FIG. 1 is a perspective diagram viewing the test chamber in an example according to the present invention from above.
Figure 2:
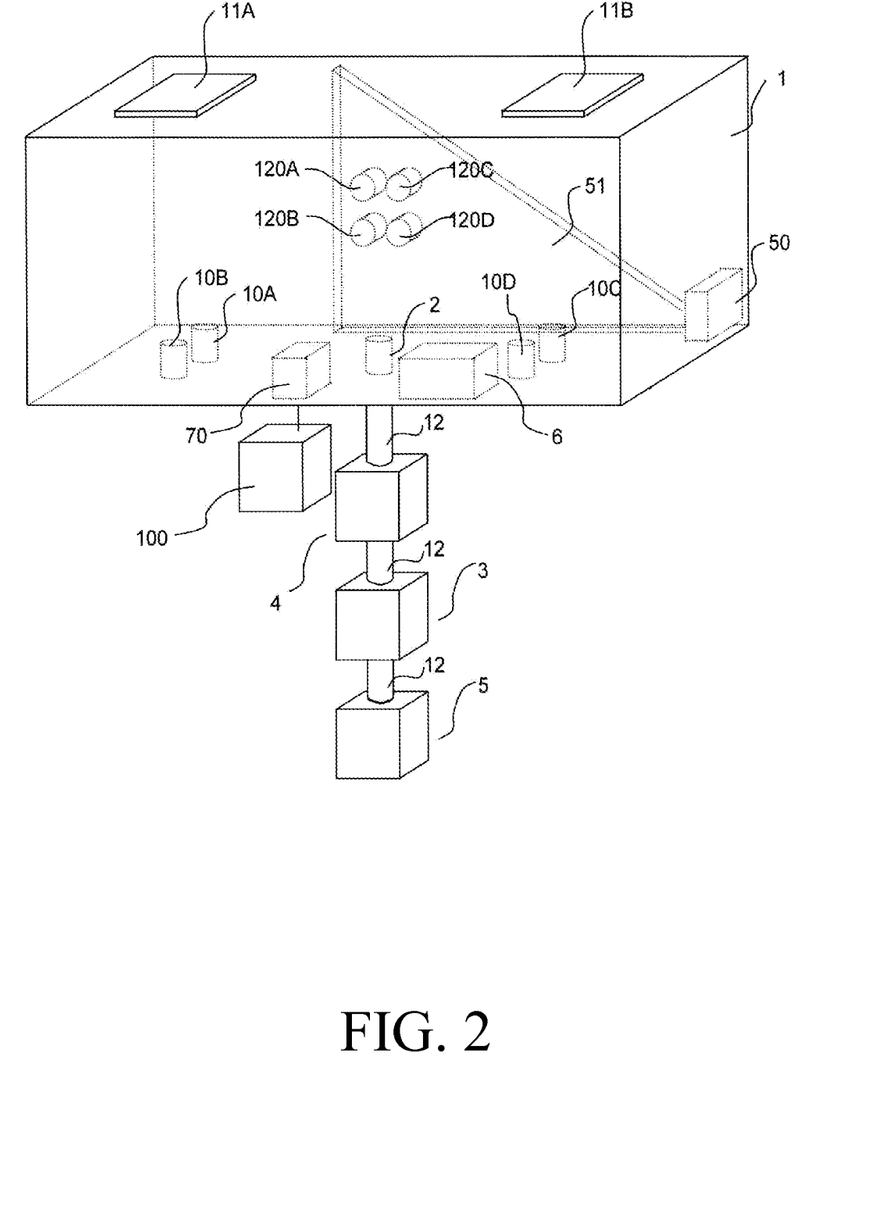
FIG. 2 is a perspective diagram viewing the test chamber in another example according to the present invention from the side.

The particle detecting device evaluating system according to the example illustrated in FIG. 1 and FIG. 2 has a test chamber 1 provided, in one face thereof, with a plurality of gas intake vents 120A, 120B, 120C, and 120D, where respective particle detecting devices 20A, 20B, 20C, and 20D are provided along the plurality of gas intake vents 120A, 120B, 120C, and 120D; an injecting device 2 for injecting particles into the test chamber 1; a light sheet forming device 50 for forming a light sheet 51 within the test chamber 1; and an imaging device 70 for imaging particles made visible by the light sheet 51.

The test chamber 1 is a chamber that is provided with, for example, an aluminum frame and transparent panels, made from polycarbonate, fitted into the frame to serve as side walls. Note that the form of the test chamber 1 may be a duct, or the like. The interior volume of the test chamber 1 is, for example, 3 m$^3$, but there is no limitation thereto. Air supplying devices 11A and 11B, for example, are provided in the test chamber 1. The air supplying devices 11A and 11B supply, into the test chamber 1, clean air through ultrahigh performance air filters such as HEPA filters (High Efficiency Particulate Filters) or ULPA filters (Ultra Low Penetration Air Filters), or the like. A door may be provided in a side wall of the test chamber 1.

The injecting device 2 is a jet-type nebulizer, and stores a fluid that includes particles having a specific concentration. Particles that are included in the fluid are microorganisms such as bacteria, funguses, viruses, allergen substances, or the like. Conversely, the particles that are included in the fluid may be, for example, non-toxic or toxic chemical substances. Conversely, the particles that are included in the fluid may be dust particles. The injecting device 2 is supplied with a gas flow, such as a compressed gas, or the like, at a specific flow rate, to produce an aerosol through spraying the fluid that contains the particles with the gas flow, to spray, in the form of a mist, the fluid that contains the particles into the test chamber 1. Note that while in the FIG. 1 and FIG. 2, the injecting device 2 is disposed within the test chamber 1, the injecting device 2 may instead be disposed on the outside of the test chamber 1, with the aerosol that is sprayed by the injecting device 2 directed into the test chamber 1 through ducting, or the like.

As illustrated in FIG. 2, the particle detecting device evaluating system according to the present example further includes a storage tank 5 for storing a compressed gas; a flow meter 3 for measuring a measured value for the flow rate of the gas flow that is provided to the injecting device 2; and a flow rate controlling device 4 for controlling, based on the measured value, the flow rate of the gas flow that is provided to the injecting device 2. The storage tank 5, the flow meter 3, the flow rate controlling device 4, and the injecting device 2 are connected by pipes 12, for example. Moreover, in order to remove particles, and the like, that are included in the compressed gas, an ultrahigh performance filter, such as a HEPA filter, or the like, is provided between the storage tank 5 and the flow rate meter 3. Note that the storage tank 5 may be replaced with a compressed gas supplying source, such as a compressor or a pump.

Figure 3:
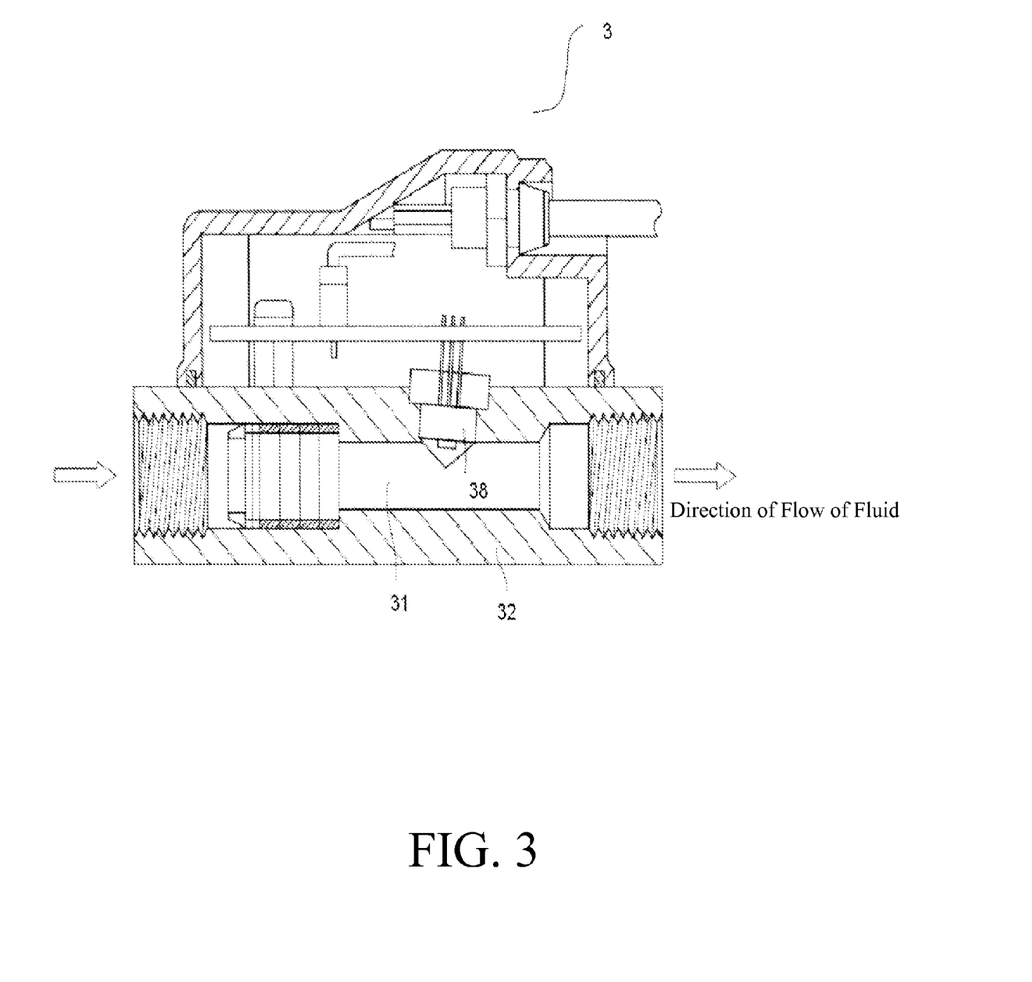
FIG. 3 is a cross-sectional diagram of a flow meter according to a further example according to the present invention.
Figure 4:
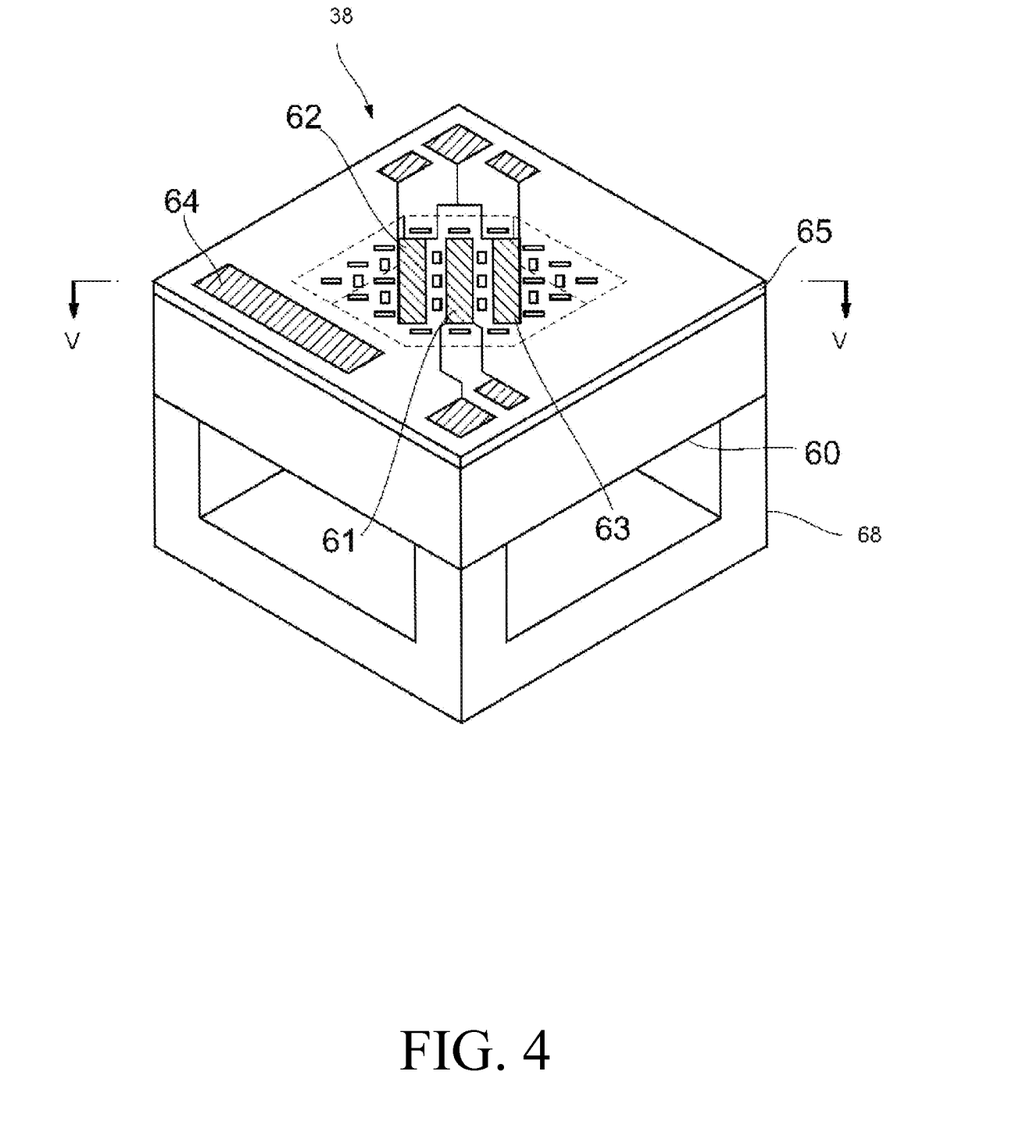
FIG. 4 is a perspective diagram of a flow sensor according to an example according to the present invention.
Figure 5:
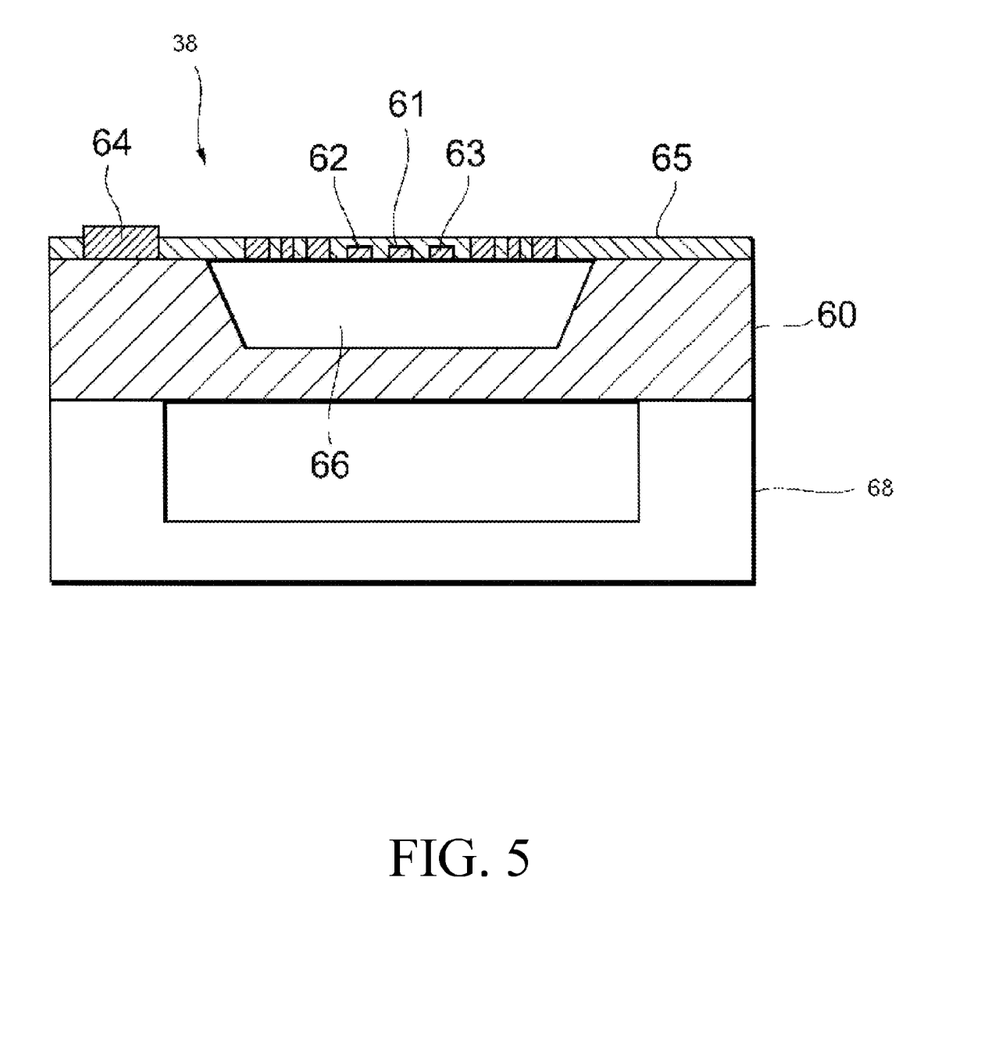
FIG. 5 is a cross-sectional diagram along the section V-V of the flow sensor illustrated in FIG. 4.

The flow meter 3 may use a mass flow meter, or the like, to measure a measured value for the flow rate of the compressed gas that is supplied from the storage tank 5. As illustrated in FIG. 3, the flow meter 3 is provided with a frame 32 in which is provided a pipe-like flow path 31 that is connected to the pipe 12, and a flow sensor 38 for detecting the flow rate of the compressed gas that flows in the flow path 31. The flow sensor 38 illustrated in FIG. 4 and FIG. 5 is a flow rate sensor or flow speed sensor, and is provided with a substrate 60, which is provided with a cavity 66, and an electrically insulating film 65 that is disposed on the substrate 60 so as to cover the cavity 66. The thickness of the substrate 60 is, for example, 0.5 mm. The length and width dimensions of the substrate 60 are, for example, 1.5 mm each. The portion of the insulating layer 65 that covers the cavity 66 forms a thermally insulating diaphragm. Moreover, the flow sensor 68 is provided with a heat generating element 61 that is provided in the diaphragm part of the insulating film 65, a first temperature measuring element 62 and a second temperature measuring element 63 that are provided at the diaphragm part of the insulating film 65 so as to have the heat generating element 61 interposed therebetween, and a temperature maintaining element 64 that is provided on the substrate 60.

The heat producing element 61 is disposed in the center of the portion of the diaphragm of the insulating layer 65 that covers the cavity 66. In the heat generating element 61 is, for example, a resistor, to generate heat through the application of electric power, to heat the compressed gas that contacts the heat generating element 61. The first temperature measuring element 62 and the second temperature measuring element 63 are electronic elements such as passive elements such as, for example, resistors, or the like, to output electric signals in accordance with the temperature of the compressed gas. The first temperature measuring element 62 and the second temperature measuring element 63 are electronic elements such as passive elements such as, for example, resistors, or the like, to output electric signals in accordance with the temperature of the compressed gas.

When the gas within the flow path 31 that is illustrated in FIG. 3 is stationary, the heat that is applied to the compressed gas from the heat generating element 61 that is illustrated in FIG. 4 and FIG. 5 can propagate symmetrically in the upstream direction and the downstream direction. Consequently, the temperatures in the first temperature measuring element 62 and the second temperature measuring element 63 can be equal, and the electrical resistances in the first temperature measuring element 62 and the second temperature measuring element 63, which are made out of platinum, or the like, can be equal. In contrast, when there is a flow of the compressed gas from upstream to downstream in the flow path 31 illustrated in FIG. 3, the heat that is applied to the compressed gas from the temperature-measuring element 61 that is illustrated in FIG. 4 and FIG. 5 can be carried in the downstream direction by the compressed gas. Consequently, the temperature of the second temperature measuring element 63 on the downstream side can be higher than the temperature of the first temperature measuring element 62 on the upstream side. Because of this, a difference can be produced between the electrical resistance of the first temperature measuring element 62 and the electrical resistance of the second temperature measuring element 63. The difference between the electrical resistance of the second temperature measuring element 63 and the electrical resistance of the first temperature measuring element 62 can be correlated with the speed of the compressed gas within the flow path 61 that is illustrated in FIG. 2. Because of this, the flow speed and flow rate of the compressed gas that flows in the flow path 31 can be calculated from the difference between the electrical resistance of the second temperature measuring element 63 and the electrical resistance of the first temperature measuring element 62.

The temperature maintaining element 64, illustrated in FIG. 4 and FIG. 5, is, for example, a resistor, which is provided with electric power to generate heat to maintain the substrate 60 at a constant temperature. Silicon (Si), or the like, may be used as the material for the substrate 60. Silicon dioxide ($SiO_2$), or the like, may be used as the material for the insulating layer 65. The cavity 66 may be formed through anisotropic etching, or the like. Furthermore, platinum (Pt) or the like may be used as the material for the first temperature measuring element 62, the second temperature measuring element 63, and the temperature maintaining element 64, and they may be formed through a lithographic method, or the like.

The flow sensor 38 is secured in the flow path 31, illustrated in FIG. 3, by a thermally insulating material 68 made from glass, or the like, that is disposed on the bottom face of the flow sensor 38. Securing the flow sensor 38 in the flow path 31 through the thermally insulating material 68 reduces the susceptibility of the temperature of the flow sensor 38 to the effects of temperature fluctuations of the inner wall of the flow path 31.

Figure 6:
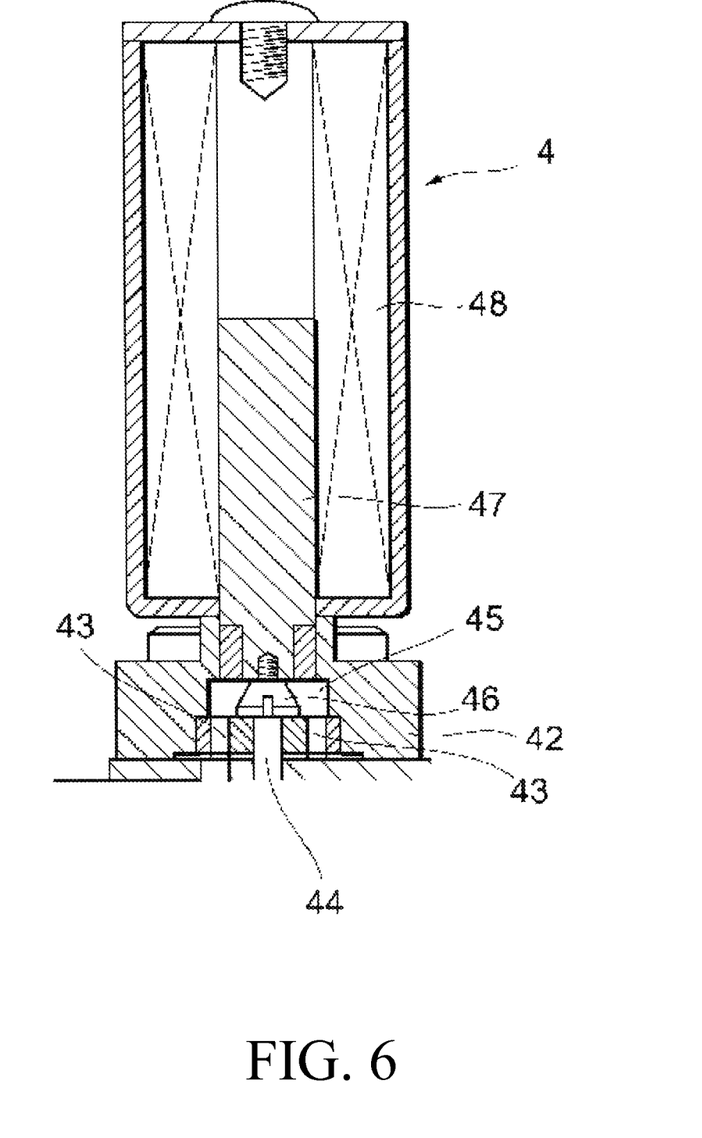
FIG. 6 is a cross-sectional diagram of a flow rate controlling device.

The flow rate controlling device 4 illustrated in FIG. 2 controls, to a prescribed value, the flow rate of the compressed gas that flows in the pipe 12, based on the measured value for the flow rate that is measured by the flow meter 3. As illustrated in FIG. 6, the flow rate controlling device 4 is provided with a valve seat that is provided with a flow path 43, a flow path 44, and a valve chamber 45 provided between the flow path 43 and the flow path 44. Moreover, the flow rate controlling device 4 is provided with a plunger 47 of a magnetic substance, a solenoid coil 48 to which an electric current is applied to drive the plunger 47 up and down, and a valve body 46, housed within the valve chamber 45, that is connected to the plunger 47 to open and close the flow path 44.

If, for example, the measured value for the flow rate of the compressed gas, measured by the flow meter 3, is greater than the prescribed value, then the flow rate controlling device 4 can apply an electric current to the solenoid coil 48, to reduce the gap between the valve body 46 and the valve seat 42, to reduce the flow rate of the compressed gas. Moreover, if the measured value for the flow rate of the compressed gas, measured by the flow meter 3, is less than the prescribed value, the flow rate controlling device 4 can apply an electric currents to the solenoid 48 to increase the gap between the valve body 46 and the valve seat 42, to increase the flow rate of the compressed gas. Doing so controls, to the vicinity of the prescribed value, the flow rate of the compressed gas that flows through the pipe 12 to be supplied to the spraying device 2. Note that while in FIG. 2 the flow rate controlling device 4 is disposed downstream from the flow meter 3, the flow rate controlling device 4 may instead be disposed upstream from the flow meter 3.

Agitating fans 10A, 10B, 10C, and 10D are disposed as agitating devices within the test chamber 1. The agitating fans 10A through 10D agitate the gas, such as air, within the test chamber 1, to prevent natural settling, by their own weight, of the particles that are dispersed into the air within the test chamber 1.

Moreover, an air cleaner 6, as a cleaning device, is disposed within the test chamber 1. The air cleaner 6 removes particles that are included in the gas, such as air, or the like, within the test chamber 1, to clean the gas. For example, the air cleaner 6 is operated prior to spraying of the fluid, which includes the particles from the injecting device 2 into the test chamber 1, to remove, from the test chamber 1, any particles other than the particles that are sprayed from the injecting device 2. Note that while in FIG. 1 and FIG. 2 the air cleaner 6 is disposed on the bottom surface within the test chamber 1, the air cleaner 6 may instead be disposed on a wall or the ceiling of the test chamber 1.

Each of the particle counter devices 20A through 20D draw in air from within the test chamber 1 to capture particles, to measure a quantity such as the number, density, or concentration of particles dispersed in the air within the test chamber 1.

The light sheet forming device 50 includes, for example, a laser for emitting a laser beam; a spherical lens for spreading the laser beam emitted by the laser; and a cylindrical lens for diffracting, in only a single direction, the laser beam that has passed through the spherical lens, to produce a laser light sheet 51. A helium neon (He—Ne) laser, an argon ion laser, a copper vapor laser, an Nd:YAG laser, an excimer laser, a semiconductor laser, or the like, may be used for the laser.

Here, if the laser light sheet 51 were not formed by the light sheet forming device 50, then, due to the scattered light of a normal beam, the particles dispersed into the air may not be brighter than the surrounding brightness due to light that is reflected from all directions. Because of this, the particles can be essentially buried in light, and thus can not be observed. In contrast, forming a laser light sheet 51 by the light sheet forming device 50, with the surroundings being dark, makes it possible to observe the particles that cut across the laser light sheet 51. The laser light sheet 51 is formed, for example, so as to be parallel to the side surface of the test chamber 1 wherein the plurality of gas intake vents 120A through 120D is provided.

A photographic camera, a digital camera, or the like, may be used as the imaging device 70 for imaging the particles that have been made visible by the light sheet 51. As illustrated in FIG. 2, a computer 100 is connected to the imaging device 70. The computer 100 has a measuring portion able to measure the quantity of particles, such as the count, density, or concentration, or the like, that have been made visible by the laser light sheet 51 and imaged by the imaging device 70. Specifically, the counting portion uses an image that is imaged by the imaging device 70 to measure the quantity of particles at a location of a given surface area corresponding to the gas intake vent 120A in the laser light sheet 51, the quantity of particles at a location of a given surface area corresponding to the gas intake vent 120B in the laser light sheet 51, the quantity of particles at a location of a given surface area corresponding to the gas intake vent 120C in the laser light sheet 51, and the quantity of particles at a location of a given surface area corresponding to the gas intake vent 120D in the laser light sheet 51.

The computer 100 is provided further with a distribution calculating portion for calculating the quantity of particles measured by the measuring portion in the vicinity of the gas intake vent 120A, the quantity of particles measured by the measuring portion in the vicinity of the gas intake vent 120B, the quantity of particles measured by the measuring portion in the vicinity of the gas intake vent 120C, and the quantity of particles measured by the measuring portion in the vicinity of the gas intake vent 120D.

As has conventionally been specified in Japan Industrial Standards (JIS) K 3836, when evaluating each of the particle detecting devices 20A through 20D, the densities of particles in a plurality of locations within the test chamber 1 are measured in advance using a light scattering-type automated particle counter, to confirm that the density distribution within the test chamber 1 is within a prescribed range. However, the present inventors discovered that even if it has been confirmed in advance that the density of particles within the test chamber 1 is uniform, non-uniformities are produced in the densities of the particles within the test chamber 1 when the plurality of particle detecting devices 20A through 20D begins drawing in the gas from within the test chamber 1 through the plurality of gas intake vents 120A through 120D.

In such a case, there can be error in the evaluation results when evaluating the respective particle capturing capabilities of the particle detecting devices 20A through 20D based on these assumption that the particle density can be uniform in the respective vicinities of the plurality of gas intake vents 120A through 120D. In contrast, the particle detecting device evaluating system according to the present example enables confirmations of whether or not the particle density is uniform in the respective vicinities of the plurality of gas intake vents 120A through 120D even after the plurality of particle detecting devices 20A through 20D has started drawing gas from within the test chamber 1.

While there are descriptions of examples as set forth above, the descriptions and drawings that form a portion of the disclosure are not to be understood to limit the present invention. A variety of alternate examples and operating technologies should be obvious to those skilled in the art. For example, while an example was given wherein the particle detecting devices 20A through 20D were disposed on the side surface of the test chamber 1, the particle detecting devices 20A through 20D may be placed instead on a bottom surface of the test chamber 1.

Additionally, the light sheet forming device 50 may form the laser light sheet 51 through reflecting the laser beam on an oscillating mirror. Conversely, the light sheet forming device 50 may form the laser light sheet 51 through reflecting the laser beam on a rotating polygon mirror. In this way, the present invention should be understood to include a variety of examples, and the like, not set forth herein.

I claim:

1. A particle detecting device evaluating system comprising:
    a test chamber provided with a face having a plurality of gas intake vents each connected to respective particle detecting devices;
    an injecting device injecting particles into the test chamber;
    a light sheet forming device forming a light sheet within the test chamber, along the plurality of the gas intake vents;
    an imaging device imaging the particles made visible by the light sheet;
    a measuring portion measuring quantities of particles made visible at a plurality of locations corresponding to the respective plurality of the gas intake vents; and a distribution calculating portion calculating distributions of the quantities of particles measured at the plurality of the locations.

2. The particle detecting device evaluating system as set forth in claim 1, further comprising:
a measuring portion measuring quantities of particles made visible in respective vicinities of the plurality of the gas intake vents.

3. The particle detecting device evaluating system as set forth in claim 2, further comprising:
a distribution calculating portion calculating distributions of the particles measured at the respective vicinities of the plurality of the gas intake vents.

4. The particle detecting device evaluating system as set forth in claim 1, wherein:
the light sheet is a laser light sheet.

5. The particle detecting device evaluating system as set forth in claim 1, further comprising:
an agitating device agitating the gas within the test chamber.

6. The particle detecting device evaluating system as set forth in claim 1, further comprising:
a cleaning device cleaning the air within the test chamber.

7. A method for evaluating a particle detecting device, comprising the steps of:
providing particle detecting devices each connected respectively to a plurality of gas intake vents that are provided on one face of a test chamber;
injecting particles into the test chamber;
forming a light sheet by a light sheet forming device, within the test chamber along the plurality of the gas intake vents;
drawing gas from within the test chamber through each of the plurality of the gas intake vents through the respective particle detecting devices;
imaging by an imaging device the particles that are made visible by the light sheet;
measuring quantities of particles made visible at a plurality of locations corresponding to the respective plurality of the gas intake vents; and
calculating distributions of the quantities of particles measured at the plurality of the locations.

8. The method for evaluating a particle detecting device as set forth in claim 7, further comprising the step of:
measuring quantities of particles made visible in respective vicinities of the plurality of the gas intake vents.

9. The method for evaluating a particle detecting device as set forth in claim 8, further comprising the step of:
calculating distributions of the quantities of particles measured in the respective vicinities of the plurality of the gas intake vents.

10. The method for evaluating a particle detecting device as set forth in claim 7, wherein:
the light sheet is a laser light sheet.

11. The method for evaluating a particle detecting device as set forth in claim 7, further comprising the step of:
agitating the gas within the test chamber.

12. The method for evaluating a particle detecting device as set forth in claim 7, further comprising the step of:
cleaning the air within the test chamber prior to injecting the particles into the test chamber.

13. A particle detecting device evaluating system comprising:
a test chamber;
an injecting device injecting particles into the test chamber;
a plurality of gas intake vents receiving the particles injected by the injecting device;
a plurality of particle detecting devices, at least one of which is disposed at each of the plurality of gas intake vents;
a light sheet forming device forming a light sheet within the test chamber, along the plurality of the gas intake vents, between the injecting device and the plurality of gas intake vents; and
an imaging device imaging the particles made visible by the light sheet.

14. A method for evaluating a particle detecting device, comprising the steps of:
injecting particles into a test chamber;
providing a plurality of gas intake vents that are provided on one face of a test chamber;
providing particle detecting devices each connected respectively to each of the plurality of gas intake vents;
forming a light sheet by a light sheet forming device, within the test chamber along the plurality of the gas intake vents between the injecting device and the plurality of gas intake vents;
drawing the particles gas from within the test chamber through each of the plurality of the gas intake vents through the respective particle detecting devices; and
imaging by an imaging device the particles that are made visible by the light sheet.

15. A particle detecting device evaluating system comprising:
a test chamber provided with a face having a plurality of gas intake vents each connected to respective particle detecting devices;
an injecting device injecting particles into the test chamber;
a light sheet forming device forming a light sheet within the test chamber, along the plurality of the gas intake vents, and illuminating the particles; and
an imaging device, disposed out of direct alignment with the light sheet forming device, imaging the particles illuminated and made visible by the light sheet.

16. A method for evaluating a particle detecting device, comprising the steps of:
providing particle detecting devices each connected respectively to a plurality of gas intake vents that are provided on one face of a test chamber;
injecting particles into the test chamber;
forming a light sheet by a light sheet forming device, within the test chamber along the plurality of the gas intake vents;
drawing gas from within the test chamber through each of the plurality of the gas intake vents through the respective particle detecting devices;
disposing an imaging device out of direct alignment with the light sheet forming device; and
imaging, by the imaging device, the particles that are made visible by the light sheet.

* * * * *